United States Patent
Zhang et al.

(10) Patent No.: US 9,193,668 B2
(45) Date of Patent: Nov. 24, 2015

(54) PROCESS FOR PRODUCING AN AMINOPROPYNE OR ENAMINONE

(75) Inventors: Yugen Zhang, Singapore (SG); Dingyi Yu, Singapore (SG); Zhewang Lin, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 14/131,083

(22) PCT Filed: Jul. 6, 2012

(86) PCT No.: PCT/SG2012/000240
§ 371 (c)(1),
(2), (4) Date: Jan. 6, 2014

(87) PCT Pub. No.: WO2013/006143
PCT Pub. Date: Jan. 10, 2013

(65) Prior Publication Data
US 2014/0142304 A1 May 22, 2014

(30) Foreign Application Priority Data

Jul. 6, 2011 (SG) .................. 201104950-9

(51) Int. Cl.
| | |
|---|---|
| *C07C 209/66* | (2006.01) |
| *C07C 213/08* | (2006.01) |
| *C07C 253/30* | (2006.01) |
| *C07C 211/27* | (2006.01) |
| *C07C 211/29* | (2006.01) |
| *C07C 211/35* | (2006.01) |
| *C07C 217/58* | (2006.01) |
| *C07C 255/58* | (2006.01) |
| *C07C 209/78* | (2006.01) |
| *C07B 37/02* | (2006.01) |
| *C07D 249/04* | (2006.01) |
| *C07D 295/023* | (2006.01) |
| *C07D 295/03* | (2006.01) |
| *C07D 249/06* | (2006.01) |

(52) U.S. Cl.
CPC .............. *C07C 209/78* (2013.01); *C07B 37/02* (2013.01); *C07C 209/66* (2013.01); *C07C 213/08* (2013.01); *C07C 253/30* (2013.01); *C07D 249/04* (2013.01); *C07D 249/06* (2013.01); *C07D 295/023* (2013.01); *C07D 295/03* (2013.01)

(58) Field of Classification Search
CPC .. C07D 401/10; C07D 417/14; C07D 471/04; C07D 403/04; C07D 403/14
See application file for complete search history.

(56) References Cited

U.S. PATENT DOCUMENTS 5,840,986 A 11/1998 Preiss et al.

FOREIGN PATENT DOCUMENTS

| JP | 2010030992 | 2/2010 |
|---|---|---|
| WO | WO-2012/005692 | 1/2012 |

OTHER PUBLICATIONS

Li et al. (chem. Commun., 2002, 268-269).*
Chernyak et al. (Angew. Chem. Int. Ed. 2010, 49, 2743-2746).*
"International Application No. PCT/SG2012/000240, International Search Report dated Sep. 17, 2012 ", 5 pgs.
Aguilar, David, et al., "Mechanistic insights into the one-pot synthesis of propargylamines from terminal alkynes and amines in chlorinated solvents catalyzed by gold compounds and nanoparticles", Chem Eur J, 16(30), (Aug. 9, 2010), 9287-96.
Feldman, Alina K, et al., "One-pot synthesis of 1,4-disubstituted 1,2,3-triazoles from in situ generated azides", Org Lett., 6(22), (Sep. 25, 2004), 3897-9.
Li, Pinhua, et al., "Iron-catalyzed ligand-free three-component coupling reactions of aldehydes, terminal alkynes, and amines", Chem Eur J, 15(9), (2009), 2045-9.
Lin, Z., et al., "Synthesis of functional acetylene derivatives from calcium carbide", ChemSusChem., 5(4), (Apr. 2012), 625-8.
Lo, Vanessa Kar-Yan, et al., "Gold(III) Salen complex-catalyzed synthesis of propargylamines via a three-component coupling reaction", Org Lett., 8(8), (Mar. 17, 2006), 1529-32.
Sreedhar, B., et al., "Ultrasound-assisted rapid and efficient synthesis of propargylamines", Tetrahedron Letters, 46(41), (Aug. 25, 2005), 7019-7022.
Wei, C., et al., "A highly efficient three-component coupling of aldehyde, alkyne, and amines via C—H activation catalyzed by gold in water.", J Am Chem Soc., 125(32), (Jul. 19, 2003), 9584-5.
Wei, Chunmei, et al., "The first silver-catalyzed three-component coupling of aldehyde, alkyne, and amine", Org Lett., 5(23), (Oct. 18, 2003), 4473-5.
Yu, Dingy!, et al., "Copper-Catalyzed Three-Component Coupling of Terminal Alkyne, Dihalomethane and Amine to Propargylic Amines", Advanced Synthesis & Catalysis, 353(1), (Jan. 10, 2011), 163-169.
Zani, Lorenzo, et al., "Dimethylzinc-mediated alkynylation of imines", J Org Chem., 71(4), (Jan. 20, 2006), 1558-62.
Zhang, W., et al., "Copper- and Amine-Free Sonogashira Reaction of N,N-Disubstituted Propargylamine: Synthesis of Substituted Aryl Propargylamine", Synthetic Communications: An International Journal for Rapid Communication of Synthetic Organic Chemistry, 36(14), (2006), 2001-2007.
Zhang, Yicheng, et al., "Indium-catalyzed highly efficient three-component coupling of aldehyde, alkyne, and amine via C—H bond activation.", J Org Chem., 74(11), (May 7, 2009), 4364-7.

* cited by examiner

*Primary Examiner* — Valerie Rodriguez-Garcia
(74) *Attorney, Agent, or Firm* — Schwegman Lundberg & Woessner, P.A.

(57) ABSTRACT

There is provided a process for producing an aminopropyne or an enaminone comprising the step of reacting a metal acetylide, an amine and a carbonyl-containing compound in the presence of a transition metal catalyst. There is also provided a process for producing an aminopropyne comprising the step of reacting a metal acetylide, an amine and a halide-containing compound in the presence of a transition metal catalyst at a reaction temperature of 50° C. to 150° C. There are also provided processes to further synthesize the aminopropyne produced to obtain a butyneamine, another aminopropyne or a triazol.

10 Claims, 1 Drawing Sheet

PROCESS FOR PRODUCING AN AMINOPROPYNE OR ENAMINONE

PRIORITY CLAIM TO RELATED APPLICATIONS

This application is a national stage application under 35 U.S.C. §371 of PCT/SG2012/000240, filed Jul. 6, 2012, and published as WO 2013/006143 A1 on Jan. 10, 2013, which claims priority to Singapore Application No. 201104950-9, filed Jul. 6, 2011, which applications and publication are incorporated by reference as if reproduced herein and made a part hereof in their entirety, and the benefit of priority of each of which is claimed herein.

TECHNICAL FIELD

The present invention generally relates to a three component coupling reaction to produce aminopropynes. The present invention also relates to a three component coupling reaction to produce enaminones.

BACKGROUND

Proparglyamines are frequent skeletons and synthetically-versatile key intermediates for the preparation of many nitrogen-containing biologically active compounds. In recent years, the most useful methods for synthesis of aminopropynes include using very sensitive Grignard reagent HCCMgBr and metal catalyzed propargylic substitution reactions with propargylic acetates, propargylic alcohols and propargylic halides. However, the organic alkynes used in aldehyde, alkyne and amine coupling or alkyne, halide and amine coupling processes are generally limited to substituted terminal alkynes, and when used, produce proparglyamines with internal alkynes which tend to limit many further important applications of functionalized alkynes.

Enaminones as synthetic chemical-intermediates have received considerable attention in recent years. This is attributed to their pronounced versatility in having the ability to participate as both electrophiles and nucleophiles in chemical reactions. While the earlier uses of enaminones were limited to serving as synthetic intermediates in organic synthesis, recent exploration for the various applications of enaminones in the valuable development of pharmaceutical products has made impressive progress.

A wide range of methods have been established to develop enaminones. Namely, these methods include condensation or addition reactions, the cleaving of heterocycles and the acylation of enaminones.

The most commonly-utilized method for the synthesis of enaminones involves the reaction between ammonia or a primary or secondary amine and a 1,3-diketone or 3-ketoester. Occasionally this strategy can fail, for example, in the use of weak bases like those of o- or p-nitroaniline.

Generally, the preceding described methods to developing enaminones or proparglyamines either require highly-specific starting materials or relatively non-facile reactive conditions to facilitate the obtainment of either the desired enaminones or proparglyamines. Furthermore, in many instances, the final product yield of enaminones or proparglyamines may not be satisfactory.

There is a need to provide a process for producing an aminopropyne (or propargylamine) that overcomes, or at least ameliorates, one or more of the disadvantages described above.

There is also a need to provide a process for producing an enaminone.

SUMMARY

According to a first aspect, there is provided a process for producing an aminopropyne comprising the step of reacting a metal acetylide, an amine and a carbonyl-containing compound in the presence of a transition metal catalyst.

Advantageously, due to the use of the metal acetylide such as calcium carbide, the produced aminopropyne may have a terminal alkyne functional group, as opposed to having the alkyne functional group within the internal structure of the aminopropyne. The terminal alkyne functional group can be used as a nucleophilic carbon source via C—H activation.

More advantageously, the use of the metal acetylide such as calcium carbide may avoid the disadvantages of the prior art such as numerous protection and de-protection steps. Accordingly, the disclosed process may greatly reduce the number of steps in the synthesis of aminopropynes. Here, the disclosed process may form the aminopropyne in a single step.

According to a second aspect, there is provided a process for producing an aminopropyne comprising the step of reacting a metal acetylide, an amine and a halide-containing compound in the presence of a transition metal catalyst at a reaction temperature of 50° C. to 150° C.

According to a third aspect, there is provided a process for producing a butyneamine comprising the steps of:

(a) reacting a metal acetylide, an amine and a carbonyl-containing compound in the presence of a transition metal catalyst to form an aminopropyne intermediate compound; and (b) adding a $C_{1-5}$-haloalkane to said aminopropyne intermediate compound of step (a) to produce said acetylamine.

According to a fourth aspect, there is provided a process for producing an aminopropyne comprising the steps of:

(a) reacting a metal acetylide, an amine and a carbonyl-containing compound in the presence of a transition metal catalyst to form an aminopropyne intermediate compound; and (b) adding a mixture of halobenzene, palladium acetate and triphenylphosphine to said aminopropyne intermediate compound of step (a) to produce said aminopropyne.

According to a fifth aspect, there is provided a process for producing a triazole comprising the steps of:

(a) reacting a metal acetylide, an amine and a carbonyl-containing compound in the presence of a transition metal catalyst to form an aminopropyne intermediate compound; and (b) adding sodium azide and any one of an aryl substituted with a halo group or a halo-$C_{1-5}$-alkane to said aminopropyne intermediate compound of step (a) to produce said triazole.

Advantageously, the disclosed process enables the butyneamine, aminopropyne and triazole to be made in a single step (ie "one-pot" manufacturing step), without additional steps such as a solvent removal step.

According to a sixth aspect, there is provided a process for producing an enaminone comprising the step of reacting a metal acetylide, an amine and an aldehyde in the presence of a transition metal catalyst.

DEFINITIONS

The following words and terms used herein shall have the meaning indicated:

The term 'alkyl' is to be interpreted broadly to refer to an alkyl radical having 1 to 5 carbon atoms. The alkyl radical may be linear or branched. The alkyl radical may be unsubstituted or may be substituted with an aryl or a halide.

The term 'alkyne' is to be interpreted broadly to refer to a functional group having the structure R—C≡C—H.

The term 'aryl' is to be interpreted broadly to refer to an aromatic hydrocarbon radical. The aryl may be unsubstituted or substituted with at least one of halide, nitrile, $C_{1-5}$-alkoxide, nitro and halo-$C_{1-5}$-alkyl. The term 'aryl' may include phenyl, monosubstituted phenyl or disubstituted phenyl.

The term 'halide' and related term 'halo' are to be interpreted broadly to refer to bromide, iodide, chloride and fluoride.

The term 'nitrile' is to be interpreted broadly to refer refers to a radical having the structure —C≡N.

The term 'alkoxide' is to be interpreted broadly to refer to a radical having the structure alkyl-O. The alkoxide may have 1 to 5 carbon atoms.

The term 'cyclic' is to be interpreted broadly to refer to a group having a non-aromatic ring structure. The cyclic group may have 3 to 6 ring atoms.

The term 'amine' is to be interpreted broadly to refer to a radical containing the NH functional group. The amine may be an aliphatic secondary amine, a cyclic secondary amine or may be a heterocyclic secondary amine. The heterocyclic secondary amine may have 5 to 6 ring atoms where the amine group is part of the ring structure. The heterocyclic secondary amine may have oxygen as one ring atom while the rest of the ring atoms (excluding the N ring atom) is carbon or all of the ring atoms (excluding the N ring atom) is carbon.

The term 'carbonyl-containing compound' is to be interpreted broadly to refer to a radical, having the C=O group. The carbonyl-containing compound may be an aldehyde or a ketone.

The term 'nitro' is to be interpreted broadly to refer to a radical of the structure —$NO_2$.

The word 'substantially' does not exclude 'completely' e.g. a composition which is 'substantially free' from Y may be completely free from Y. Where necessary, the word 'substantially' may be omitted from the definition of the invention.

Unless specified otherwise, the terms 'comprising' and 'comprise', and grammatical variants thereof, are intended to represent 'open' or 'inclusive' language such that they include recited elements but also permit inclusion of additional, unrecited elements.

As used herein, the term 'about', in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Exemplary, non-limiting embodiments of a process for producing an aminopropyne will now be disclosed.

The process may comprise the step of reacting a metal acetylide, an amine and a carbonyl-containing compound in the presence of a transition metal catalyst.

The process may comprise the step of reacting a metal acetylide, an amine and a halide-containing compound in the presence of a transition metal catalyst. This process may be undertaken at a reaction temperature of about 70° C. to about 90° C.

The process may result in the production of an aminopropyne with a terminal alkyne group. Hence, the presence of the terminal alkyne group may allow the aminopropyne to be used as a nucleophilic carbon source via C—H activation.

The metal acetylide may have the structure $MC_2$ (that is, M-C≡C), where M is a metal selected from the group consisting of an alkali metal, an alkaline earth metal and a transition metal. M may be selected from lithium, calcium or lanthanum and hence the metal carbide salt may be selected from the group consisting of calcium carbide ($CaC_2$), lithium acetylide ($Li_2C_2$) and lanthanum acetylide ($LaC_2$).

The transition metal catalyst may be a transition metal salt. The transition metal may be selected from Group IB of the Periodic Table of Elements and hence, may be selected from the group consisting of copper, silver and gold.

The copper may be present as copper (I) or copper (II) and hence, the copper catalyst may be selected from the group consisting of copper halide (such as copper chloride (CuCl or $CuCl_2$), copper bromide (CuBr or $CuBr_2$), copper iodide (CuI or $CuI_2$) and copper fluoride (CuF or $CuF_2$)), copper acetate ($Cu(OAc)_2$) and copper acetylacetonate ($Cu(acac)_2$).

The carbonyl-containing compound may be an aldehyde having the structure $R_1CHO$, where $R_1$ is selected from aryl or $C_{1-5}$-alkyl, said aryl being optionally substituted by at least one of halide, nitrile, nitrile, $C_{1-5}$-alkyl, $C_{1-5}$-alkoxide, nitro and halo-$C_{1-5}$-alkyl (such as trihalo-$C_{1-5}$-alkyl) and said $C_{1-5}$-alkyl being optionally substituted by phenyl. The aldehyde may be benzaldehyde optionally substituted with one or two substituents independently selected from the group consisting of a halide such as chloride, fluoride, iodide or bromide, nitrile, methyl, ethyl, propyl, butyl, pentyl, methoxide, ethoxide, propoxide, butoxide, pentoxide, nitro, trifluoromethyl, trichloromethyl, triiodomethyl or tribromoalkyl. The aldehyde may be linear or branched ethanal, propanal, butanal, pentanal and hexanal, which may in turn be optionally substituted with a phenyl group. The branched aldehyde may be 2-methylpropanal. The aldehyde may be benzenepropanal.

The carbonyl-containing compound may be a ketone having the structure $R_2CO$, where $R_2$ is, selected from cyclic-$C_{3-6}$-alkyl. The ketone may be selected from the group consisting of cyclopropanone, cyclobutanone, cyclopentanone and cyclohexanone.

The amine may be a secondary amine. The secondary amine may have the structure $R_3R_4NH$, where $R_3$ and $R_4$ are independently selected from $C_{1-5}$-alkyl. Hence, the secondary amine may be dimethylamine, methylethylamine, diethylamine, methylpropylamine, methylbutylamine, diisopropylamine or ethylpropylamine. The secondary amine may be a heterocyclic secondary amine having 5 to 6 ring atoms. The heterocyclic secondary amine may be pyrrolidine, piperidine and morpholine. The amine may not be a primary amine.

The process may be undertaken at a temperature selected from about 50° C. to about 150° C., about 50° C. to about 60° C., about 50° C. to about 70° C., about 50° C. to about 80° C., about 50° C. to about 90° C., about 50° C. to about 100° C., about 50° C. to about 110° C., about 50° C. to about 120° C., about 50° C. to about 130° C., about 50° C. to about 140° C., about 60° C. to about 150° C., about 70° C. to about 150° C., about 80° C. to about 150° C., about 90° C. to about 150° C., about 100° C. to about 150° C., about 110° C. to about 150° C., about 120° C. to about 150° C., about 130° C. to about 150° C., about 140° C. to about 150° C. and about 70° C. to about 90° C. The reaction temperature may be about 80° C. or about 120° C.

The process may be undertaken for a period of time that is sufficient for all of at least one of the reactants (metal acetylide, amine, carbonyl-containing compound or alternatively halide-containing compound) to be consumed. The reaction time may depend in part on the temperature used for the reaction. The reaction time may be from about 18 hours to about 120 hours, about 18 hours to about 24 hours, about 18 hours to about 48 hours, about 18 hours to about 72 hours, about 18 hours to about 96 hours, about 24 hours to about 120 hours, about 48 hours to about 120 hours, about 72 hours to about 120 hours and about 96 hours to about 120 hours. The reaction time may be about 18 hours, about 24 hours, about 72 hours or about 120 hours.

The amount of the catalyst (relative to the carbonyl-containing compound) in the reaction may be from about 5 mol % to about 15 mol %, about 5 mol % to about 6 mol %, about 5 mol % to about 7 mol %, about 5 mol % to about 8 mol %, about 5 mol % to about 9 mol %, about 5 mol % to about 10 mol %, about 5 mol % to about 11 mol %, about 5 mol % to about 12 mol %, about 5 mol % to about 13 mol %, about 5 mol % to about 14 mol %, about 6 mol % to about 15 mol %, about 7 mol % to about 15 mol %, about 8 mol % to about 15 mol %, about 9 mol % to about 15 mol %, about 10 mol % to about 15 mol %, about 11 mol % to about 15 mol %, about 12 mol % to about 15 mol %, about 13 mol % to about 15 mol %, and about 14 mol % to about 15 mol %. The amount of the catalyst relative to the carbonyl-containing compound may be about 10 mol %.

The molar ratio of the metal acetylide to the carbonyl-containing compound may be about 0.5 to about 1.5 (that is, about 0.5:1 to about 1.5:1). The molar ratio of the metal acetylide to the carbonyl-containing compound may be about 0.5 to about 1.5, about 0.5 to about 0.6, about 0.5 to about 0.7, about 0.5 to about 0.8, about 0.5 to about 0.9, about 0.5 to about 1.0, about 0.5 to about 1.1, about 0.5 to about 1.2, about 0.5 to about 1.3, about 0.5 to about 1.4, about 0.6 to about 1.5, about 0.7 to about 1.5, about 0.8 to about 1.5, about 0.9 to about 1.5, about 1.0 to about 1.5, about 1.1 to about 1.5, about 1.2 to about 1.5, about 1.3 to about 1.5, about 1.4 to about 1.5 and about 1.3 to about 1.4. The molar ratio of the metal acetylide to the carbonyl-containing compound may be about 1.2:1. Representative amounts of the metal acetylide and the carbonyl-containing compound may be 1.2 mmol and 1 mmol respectively.

The molar ratio of the amine to the carbonyl-containing compound may be about 1 to about 2 (that is, about 1:1 to about 2:1). The molar ratio of the amine to the carbonyl-containing compound may be about 1 to about 2, about 1.1 to about 2, about 1.2 to about 2, about 1.3 to about 2, about 1.4 to about 2, about 1.5 to about 2, about 1.6 to about 2, about 1.7 to about 2, about 1.8 to about 2, about 1.9 to about 2, about 1 to about 1.1, about 1 to about 1.2, about 1 to about 1.3, about 1 to about 1.4, about 1 to about 1.5, about 1 to about 1.6, about 1 to about 1.7, about 1 to about 1.8, about 1 to about 1.9 and about 1.4 to about 1.6. The molar ratio of the amine to the carbonyl-containing compound may be about 1.5:1. Representative amounts of the amine and the carbonyl-containing compound may be 1.5 mmol and 1 mmol respectively.

The process may comprise the step of adding a solvent to the reaction mixture. The solvent may be an aprotic solvent. The solvent may be polar or may be non-polar. The solvent may be inert to the reaction conditions or one or more of the reactants may be used as the solvent. The solvent may be selected from the group consisting of acetonitrile, tetrahydrofuran, toluene, pyridine and mixtures thereof. The solvent may be a dry solvent, that is, an anhydrous solvent. The solvent may contain water and may be termed as an "undried solvent". The amount of water in the solvent may be from about 0.01 vol % to about 1 vol %, about 0.1 vol % to about 1 vol %, about 0.2 vol % to about 1 vol %, about 0.3 vol % to about 1 vol %, about 0.4 volt to about 1 vol %, about 0.5 vol % to about 1 vol %, about 0.6 vol % to about 1 vol %, about 0.7 vol % to about 1 volt, about 0.8 vol % to about 1 vol %, about 0.9 vol % to about 1 vol %, about 0.01 vol % to about 0.1 vol %, about 0.01 vol % to about 0.2 vol %, about 0.01 vol % to about 0.3 volt, about 0.01 vol % to about 0.4 vol %, about 0.01 vol % to about 0.5 vol %, about 0.01 vol % to about 0.6 vol %, about 0.1 vol % to about 0.7 vol %, about 0.1 vol % to about 0.8 vol % and about 0.1 vol % to about 0.9 vol %. The water content in the solvent may be about 0.02 vol %, which is equivalent to 2 mol % of the carbonyl-containing compound. Due to the trace amount of water in the solvent, this may help to break down the polymeric structure of the metal acetylide such as calcium carbide. Hence, this may aid in speeding up the reaction so as to shorten the reaction time.

The process may comprise the step of adding a base to the reaction mixture. The base may be an inorganic base or an organic base. The base may be selected from the group consisting of a carbonate, a bicarbonate, a phosphate and an amine. In some instances, the amine of the reaction may also function as a base. An excess of that amine may be used in such cases. Alternatively, a separate amine which cannot participate in the reaction may be used. Such amines include anilines, secondary aromatic amines and tertiary amines. Suitable amines which may be used as the base may be selected from the group consisting of diazabicyclononene, diazabicycloundecene, triethylamine, pyridine and α-methyl benzylamine. The base may be soluble in the solvent or it may be insoluble in the solvent, or it may be sparingly soluble in the solvent. The base, if used, may be soluble in the solvent or may be insoluble therein. In some instances, the selection of base can control the product obtained. For example, in the AHA-coupling process, use of an inorganic base may result in disubstitution to produce an aminopropyne with an internal alkyne structure while use of an organic base (or no added base) may result in monosubstitution to produce an aminopropyne with a terminal alkyne. This can be shown in the scheme below when calcium carbide, dichloromethane and diisopropylamine were mixed with CuCl in different types of base to form either diisopropylaminopropyne (B1) or the corresponding symmetric bis-substituted propargylic amine product with internal alkyne structure (B2).

Scheme 1

The process may be undertaken in an inert atmosphere.

The aminopropyne produced from the process using reactants such as the metal acetylide, amine and carbonyl-containing compound may be of the formula H—C≡C—C(A)-N(B), where A refers to the substituent(s) of the carbonyl-containing compound and B refers to the substituent(s) of the amine.

The halide-containing compound may be a $C_{1-5}$ haloalkane. The $C_{1-5}$-haloalkane may be $C_{1-5}$-dihaloalkane. The halide-containing compound may be selected from the group consisting of dihalomethane, dihaloethane, dihalopropane, dihalobutane or dihalopentane, where halo may be chlorine, fluoride, bromine or iodine. The halide-containing compound may be benzal halide. The halide-containing compound may be selected from the group consisting of dichloromethane, dichloroethane, dichloropropane, dichlorobutane, dichloropentane, diiodomethane, diiodoethane, diiodopropane, diiodobutane, diiodopentane, dibromomethane, dibromoethane, dibromopropane, dibromobutane, dibromopentane, difluoromethane, difluoroethane, difluoropropane, difluorobutane, difluoropentane, benzal chloride, benzal iodide, benzal bromide and benzal fluoride.

The aminopropyne produced from the process using reactants such as the metal acetylide, amine and carbonyl-containing compound may be of the formula H—C≡C—C(A)-N(B), where A represents the substituent(s) of the carbonyl-containing compound and B represents the substituent(s) of the amine. This process is also termed as AAA-coupling.

The aminopropyne produced from the process using reactants such as the metal acetylide, amine and halide-containing compound may be of the formula H—C≡C—C(D)-N(B), where D represents the substituent(s) of the halide-containing compound and B represents the substituent(s) of the amine. This process is also termed as AHA coupling.

An exemplary reaction scheme showing the AAA-coupling and AHA-coupling is shown below where calcium carbide is used as the metal acetylide.

Scheme 2

The yield of the aminopropyne produced from the process may be at least 30%, 40%, 50%, 60%, 70%, 80% or 90%.

The produced aminopropyne may be used to synthesize a butyneamine. The butyneamine may be a butynediamine. Following the above AAA-coupling, a $C_{1-5}$-haloalkane may be added to form an asymmetric bis-substituted butynediamine. The butynediamine may be produced in a single reaction vessel or "one-pot". The $C_{1-5}$-haloalkane may be as described above. An exemplary process to form a butynediamine may include reacting calcium carbide, benzaldehyde, diisopropylamine, CuI and $CH_3CN$ for 18 hours at 80° C. (AAA-coupling), followed by addition of dichloromethane and stirred for another 24 hours at 80° C. to obtain an asymmetric bis-substituted product, $N^1,N^1,N^4,N^4$-tetraisopropyl-1-phenylbut-2-yne-1,4-diamine with 70% isolated yield. A scheme of this reaction (also termed as AAA-AHA coupling) is shown below.

Scheme 3

70% isolated yield

Hence, the process for producing a butyneamine may comprise the steps of:

(a) reacting a metal acetylide, an amine and a carbonyl-containing compound in the presence of a transition metal catalyst to form an aminopropyne intermediate compound; and (b) adding a $C_{1-5}$-haloalkane to said aminopropyne intermediate compound of step (a) to produce said butyneamine.

The produced aminopropyne may be used as an intermediate to synthesize another aminopropyne product. In another embodiment, after the AAA-coupling, a mixture of halobenzene, palladium acetate and triphenylphosphine may be added to form an aminopropyne. The aminopropyne may be produced in a single reaction vessel or "one-pot". An exemplary process to form an aminopropyne may include reacting calcium carbide, benzaldehyde, diethylamine, CuI and CH₃CN for 18 hours at 80° C. (AAA-coupling), followed by addition of iodobenzene, palladium acetate and triphenylphosphine and stirred for another 10 hours at 60° C. to obtain N,N,-diethyl-1,3-diphenylprop-2-yn-1-amine with 60% isolated yield. A scheme of this reaction (also termed as AAA-Sonogashira coupling) is shown below.

Hence, the process for producing an aminopropyne may comprise the steps of:

(a) reacting a metal acetylide, an amine and a carbonyl-containing compound in the presence of a transition metal catalyst to form an intermediate compound; and (b) adding a mixture of halobenzene, palladium acetate and triphenylphosphine to said aminopropyne intermediate compound to produce said aminopropyne. The halobenzene may be selected from the group consisting of fluorobenzene, chlorobenzene, iodobenzene and bromobenzene.

The process may comprise the step of selecting a temperature of from about 50° C. to about 90° C., about 50° C. to about 60° C., about 50° C. to about 70° C., about 50° C. to about 80° C., about 60° C. to about 90° C., about 70° C. to about 90° C. and about 80° C. to about 90° C., in step (b) of the above process. The temperature in step (b) of the process may be abut 80° C. or may be about 60° C.

The produced aminopropyne may be used to synthesize a triazole product. This process may involve AAA-coupling in the first step followed by click chemistry with sodium azide with either an aryl substituted with a halo group or a halo-C₁₋₅-alkane. A scheme of this reaction (also termed as AAA-click chemistry) is shown below.

An exemplary process to form a triazole product may include reacting calcium carbide, benzaldehyde, diethylamine, CuI and CH₃CN for 18 hours at 80° C. (AAA-coupling), followed by addition of sodium azide, iodobenzene, CuI and N,N-dimethylethylenediamine in dimethyl formamide and stirred for 12 hours at 40° C. to obtain N-ethyl-N-(phenyl(1-phenyl-1H-1,2,3-triazol-4-yl)methyl)ethanamine after extraction and purification with 84% isolated yield.

Hence, the process for producing an triazole may comprise the steps of:

(a) reacting a metal acetylide, an amine and a carbonyl-containing compound in the presence of a transition metal catalyst to form an aminopropyne intermediate compound; and (b) adding sodium azide with one of an aryl substituted with a halo group or a halo-C₁₋₅-alkane to said aminopropyne intermediate compound of step (a) to produce said triazol.

The yield of the triazole product may be at least about 30%, 40%, 50%, 60%, 70%, 80% or 90%.

Exemplary, non-limiting embodiments of a process for producing an enaminone will now be disclosed.

The process comprises the step of reacting a metal acetylide, an amine and an aldehyde in the presence of a transition metal catalyst.

The process may comprise the step of adding a solvent to the reacting step. The solvent may be selected to induce formation of an enaminone from the reactants stated above. The solvent may be a formamide (such as dimethyl formamide) or a sulphoxide (such as dimethyl sulphoxide). The solvent may include water in an amount from about 0.5 to about 1.5%, about 0.5 to about 0.6%, about 0.5 to about 0.7%, about 0.5 to about 0.8%, about 0.5 to about 0.9%, about 0.5 to about 1%, about 0.5 to about 1.1%, about 0.5 to about 1.2%, about 0.5 to about 1.3%, about 0.5 to about 1.4%, about 0.6 to about 1.5%, about 0.7 to about 1.5%, about 0.8 to about 1.5%, about 0.9 to about 1.5%, about 1 to about 1.5%, about 1.1 to about 1.5%, about 1.2 to about 1.5%, about 1.3 to about 1.5%, about 1.4 to about 1.5%, about 0.9 to about 1.1%. The amount of water in the solvent may be about 1%.

The metal acetylide may have the structure $MC_2$ (that is, $M-C\equiv C$), where M is a metal selected from the group consisting of an alkali metal, an alkaline earth metal and a transition metal. M may be selected from lithium, calcium or lanthanium and hence the metal carbide salt may be selected from the group consisting of calcium carbide ($CaC_2$), lithium acetylide ($Li_2C_2$) and lanthanium acetylide ($LaC_2$).

The transition metal catalyst may be a transition metal salt. The transition metal may be selected from Group IB of the Periodic Table of Elements and hence, may be selected from the group consisting of copper, silver and gold.

The copper may be present as copper (I) or copper (II) and hence, the copper catalyst may be selected from the group consisting of copper halide (such as copper chloride (CuCl or $CuCl_2$), copper bromide (CuBr or $CuBr_2$), copper iodide (CuI or $CuI_2$) and copper fluoride (CuF or $CuF_2$)), copper acetate ($Cu(OAc)_2$) and copper acetylacetonate ($Cu(acac)_2$).

The aldehyde may have the structure $R_1\text{,CHO}$, where $R_1$, is selected from aryl, said aryl being optionally substituted by at least one of halide, nitrile, $C_{1-5}$-alkoxide, nitro and halo-$C_{1-5}$-alkyl (such as trihalo-$C_{1-5}$-alkyl). The aldehyde may be benzaldehyde optionally substituted with one or two substituents independently selected from the group consisting of a halide such as chloride, fluoride, iodide or bromide, nitrile, methyl, ethyl, propyl, butyl, pentyl, methoxide, ethoxide, propoxide, butoxide, pentoxide, nitro, trifluoromethyl, trichloromethyl, triiodomethyl or tribromoalkyl.

The amine may be a secondary amine. The amine may be selected to induce formation of an enaminone. Hence, the solvent and amine may be selected to induce formation of an enaminone. In order to form enaminone, the amine may have at least one substituent which is bulkier (in terms of steric bulk) than a methyl group or an ethyl group. The amine may be more bulkier than diethylamine. The secondary amine may have the structure $R_5R_6NH$, where $R_5$ and $R_6$ are independently selected from $C_{1-5}$-alkyl and cyclo-$C_{3-6}$-alkyl. Hence, the secondary amine may be dimethylamine, methylethylamine, diethylamine, diisopropylamine, methylpropylamine, ethylisopropylamine, methylisopropylamine, methylbutylamine, ethylpropylamine or dicyclohexylamine. The amine may be a heterocyclic secondary amine having 5 to 6 ring atoms. The heterocyclic secondary amine may be pyrrolidine, piperidine and morpholine.

The process may be undertaken at a temperature selected from about 50° C. to about 150° C., about 50° C. to about 60° C., about 50° C. to about 70° C., about 50° C. to about 80° C., about 50° C. to about 90° C., about 50° C. to about 100° C., about 50° C. to about 110° C., about 50° C. to about 120° C., about 50° C. to about 130° C., about 50° C. to about 140° C., about 60° C. to about 150° C., about 70° C. to about 150° C., about 80° C. to about 150° C., about 90° C. to about 150° C., about 100° C. to about 150° C., about 110° C. to about 150° C., about 120° C. to about 150° C., about 130° C. to about 150° C., about 140° C. to about 150° C. and about 80° C. to about 90° C. The reaction temperature may be about 85° C. or about 950° C.

The process may be undertaken for a period of time that is sufficient for all of at least one of the reactants (metal acetylide, amine and aldehyde) to be consumed. The reaction time may depend in part on the temperature used for the reaction. The reaction time may be from about 10 hours to about 50 hours, about 10 hours to about 20 hours, about 10 hours to about 30 hours, about 10 hours to about 40 hours, about 40 hours to about 50 hours, about 30 hours to about 50 hours, about 20 hours to about 50 hours, about 15 hours to about 20 hours, about 45 hours to about 50 hours. The reaction time may be about 16 hours or about 48 hours.

The amount of the catalyst (relative to the aldehyde) in the reaction may be from about 5 mol % to about 15 mol %, about 5 mol % to about 6 mol %, about 5 mol % to about 7 mol %, about 5 mol % to about 8 mol %, about 5 mol % to about 9 mol %, about 5 mol % to about 10 mol %, about 5 mol % to about 11 mol %, about 5 mol % to about 12 mol %, about 5 mol % to about 13 mol %, about 5 mol % to about 14 mol %, about 6 mol % to about 15 mol %, about 7 mol % to about 15 mol %, about 8 mol % to about 15 mol %, about 9 mol % to about 15 mol %, about 10 mol % to about 15 mol %, about 11 mol % to about 15 mol %, about 12 mol % to about 15 mol %, about 13 mol % to about 15 mol %, and about 14 mol % to about 15 mol %. The amount of the catalyst relative to the aldehyde may be about 5 mol %.

The molar ratio of the metal acetylide to the aldehyde may be about 0.5 to about 1.5 (that is, about 0.5:1 to about 1.5:1). The molar ratio of the metal acetylide to the aldehyde may be about 0.5 to about 1.5, about 0.5 to about 0.6, about 0.5 to about 0.7, about 0.5 to about 0.8, about 0.5 to about 0.9, about 0.5 to about 1.0, about 0.5 to about 1.1, about 0.5 to about 1.2, about 0.5 to about 1.3, about 0.5 to about 1.4, about 0.6 to about 1.5, about 0.7 to about 1.5, about 0.8 to about 1.5, about 0.9 to about 1.5, about 1.0 to about 1.5, about 1.1 to about 1.5, about 1.2 to about 1.5, about 1.3 to about 1.5, about 1.4 to about 1.5 and about 1.3 to about 1.4. The molar ratio of the metal acetylide to the aldehyde may be about 1.2:1. Representative amounts of the metal acetylide and the aldehyde may be 1.2 mmol and 1 mmol respectively.

The molar ratio of the amine to the aldehyde may be about 1 to about 2 (that is, about 1:1 to about 2:1). The molar ratio of the amine to the aldehyde may be about 1 to about 2, about 1.1 to about 2, about 1.2 to about 2, about 1.3 to about 2, about 1.4 to about 2, about 1.5 to about 2, about 1.6 to about 2, about 1.7 to about 2, about 1.8 to about 2, about 1.9 to about 2, about 1 to about 1.1, about 1 to about 1.2, about 1 to about 1.3, about 1 to about 1.4, about 1 to about 1.5, about 1 to about 1.6, about 1 to about 1.7, about 1 to about 1.8, about 1 to about 1.9 and about 1.4 to about 1.6. The molar ratio of the amine to the aldehyde may be about 1.5:1. Representative amounts of the amine and the aldehyde may be 1.5 mmol and 1 mmol respectively.

The process may be undertaken in an inert atmosphere.

The enaminone produced from this process may be of the formula $R_1C(=O)C=CNR_5R_6$, where $R_1$ represents the substituent of the aldehyde and $R_5$ and $R_6$ represent the substituents of the amine.

Enaminones

The yield of the enaminone produced from the process may be at least 30%, 40%, 50%, 60%, 70%, 80% or 90%.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

EXAMPLES

Non-limiting examples of the invention will be further described in greater detail by reference to specific Examples, which should not be construed as in any way limiting the scope of the invention.

Materials and Methods

All solvents were purchased from Aldrich or Fluka. All starting materials are commercially available and were used as received, unless otherwise indicated. Reactions were monitored by thin layer chromatography using 0.25-mm E. Merck silica gel coated glass plates (60E-254) with UV light to visualize the course of reaction. Chemical yields referred to the pure isolated substances. Gas chromatography-mass spectrometry (GC-MS) was performed with Shimadzu GC-2010 coupled with GCMS-QP2010. $^1$H and $^{13}$C NMR spectra were obtained using a Brucker AV-400 (400 MHz) spectrometer. Chemical shifts were reported in ppm from tetramethylsilane with the solvent resonance as the internal standard. Data were reported in the following order: chemical shift in ppm (δ) (multiplicity were indicated by br (broadened), s (singlet), d (doublet), t (triplet), q (quartet), m (multiplet), $m_c$ (centered multiplet)); coupling constants (J, Hz); integration; assignment.

Example 1

Production of Aminopropyne by AHA-Coupling

In general, a mixture of calcium carbide (1.0 mmol), dichloromethane (1.5 mmol), diisopropylamine (1.5 mmol), and copper halide catalyst (0.1 mmol) was added in a reaction tube (10 mL) with 2 mL CH$_3$CN. Where required, a base (2.4 mmol) was also added. After stirring at a certain temperature for a certain period of time, the mixture was diluted with H$_2$O (10 mL), the aqueous layers were extracted with diethyl ether (2×10 mL), dried over Na$_2$SO$_4$ and concentrated under vacuum to give the crude product which was further purified by column chromatography on silica gel (ethyl acetate/hexane=1:1) to afford the corresponding pure aminopropyne, which is N,N-diisopropyl-2-yn-1-amine (B1) and N$^1$,N$^1$,N$^4$,N$^4$-tetraisopropylbut-2-yne-1,4-diamine (B2). The different types of catalyst and base as well as the different reaction times and temperatures are shown in Table 1 below. Both products gave satisfactory spectroscopic data.

TABLE 1

| Entry | Catalyst (mol %) | Base | Reaction Time (hours) | Temperature (° C.) | Yield (%) B1 | Yield (%) B2 |
|---|---|---|---|---|---|---|
| 1 | CuCl (10) | — | 72 | 80 | 70 | 0 |
| 2 | CuBr (10) | — | 72 | 80 | 72 | — |
| 3 | CuCl (10) | — | 72 | 120 | 72 | 0 |
| 4 | CuCl (10) | — | 24 | 80 | 20 | 0 |
| 5 | CuCl (10) | — | 120 | 80 | 75 | 0 |
| 6 | CuCl (10) | TEA | 72 | 80 | 70 | 0 |
| 7 | CuCl (10) | DIEA | 72 | 80 | 65 | 0 |
| 8$^a$ | CuCl (10) | K$_2$CO$_3$ | 72 | 80 | 0 | 70 |
| 9$^a$ | CuCl (10) | Cs$_2$CO$_3$ | 72 | 80 | 0 | 75 |

$^a$calcium carbide (1.0 mmol), dichloromethane (3 mmol), diisopropylamine (3 mmol).

Different types of amine were also tested as shown in Table 2 below. Unless otherwise stated, the reaction conditions are: 10 mol % copper chloride (CuCl) catalyst, dichloromethane (1.5 mmol) with CH$_3$CH, reaction time was 72 hours and reaction temperature was 80° C.

TABLE 2

| Entry | Amine | Product | | Yield |
|---|---|---|---|---|
| 1 | (diisopropylamine) | (propynyl diisopropylamine) | N,N-diisopropyl-2-yn-1-amine (C1) | 70% |
| 2 | (morpholine) | (propynyl morpholine) | 4-(prop-2-ynyl) morpholine (C2) | 70% |
| 3 | (pyrrolidine) | (propynyl pyrrolidine) | 1-(prop)-2-ynyl) pyrrolidine (C3) | 75% |

Example 2

Production of Aminopropyne by AAA-Coupling

A mixture of calcium carbide (1.2 mmol), a benzaldehyde (1.0 mmol), diisopropylamine (1.5 mmol), and copper halide catalyst (0.1 mmol) was added in a reaction tube (10 mL) with 2 mL of anhydrous solvent. After stirring at a certain temperature for a certain period of time, the mixture was diluted with $H_2O$ (10 mL), the aqueous layers were extracted with diethyl ether (2×10 mL), dried over $Na_2SO_4$ and concentrated under vacuum to give the crude product which was further purified by column chromatography on silica gel (ethyl acetate/hexane=4:1) to afford the corresponding pure aminopropyne. The different types of catalyst and solvent as well as the different reaction times and temperatures are shown in Table 3 below. All products gave satisfactory spectroscopic data.

TABLE 3

| Entry | Catalyst (mol %) | Solvent | Reaction Time (hours) | Temperature (° C.) | Yield (%) |
|---|---|---|---|---|---|
| 1 | CuCl (10) | $CH_3CN$ | 72 | 80 | 50 |
| 2 | $CuCl_2$ (10) | $CH_3CN$ | 72 | 80 | 5 |
| 3 | CuBr (10) | $CH_3CN$ | 72 | 80 | 70 |
| 5 | CuI (10) | $CH_3CN$ | 72 | 80 | 72 |
| 6[a] | CuI (10) | $CH_3CN$[a] | 18 | 80 | 69 |
| 7 | $Cu(acac)_2$ (10) | $CH_3CN$ | 72 | 80 | 5 |
| 8 | $Cu(OAc)_2$ (10) | $CH_3CN$ | 72 | 80 | 60 |
| 9 | CuI (10) | THF | 72 | 80 | 10 |
| 10 | CuI (10) | Toluene | 72 | 80 | 5 |
| 11 | CuI (10) | Pyridine | 72 | 80 | 5 |
| 12 | CuI (10) | $CH_3CN$ | 24 | 80 | 25 |
| 13 | CuI (10) | $CH_3CN$ | 120 | 80 | 72 |
| 14 | CuI (10) | $CH_3CN$ | 72 | 120 | 70 |

[a]Undried $CH_3CN$ (2 mol), 80° C., 18 hours.

Different types of aldehyde/ketone as well as amine were also tested as shown in Table 4 below. Unless otherwise stated, the catalyst used was 10 mol % copper iodide (CuI), solvent was undried $CH_3CN$ (2 mol), reaction time was 18 hours and the reaction temperature was 80° C.

TABLE 4

| Entry | Aldehyde/Ketone | Amine | Yield[a] (%) | Product | |
|---|---|---|---|---|---|
| 1 | benzaldehyde | H—N(Et)₂ | 86 | | N,N-diethyl-1-phenylprop-2-yn-1-amine (D1) |

TABLE 4-continued

$$\text{Ca}-\text{C}\equiv\text{C} + \underset{R_1}{\overset{O}{\underset{\|}{C}}}\!\!-\!\!R_2 + \text{HN}\!\!<\!\!\overset{R_3}{\underset{R_4}{}} \xrightarrow[\text{Undried CH}_3\text{CN}]{10 \text{ mol \% CuI, } 80°\text{C.}} \text{H}\!-\!\text{C}\!\equiv\!\text{C}\!-\!\underset{\underset{N<R_3/R_4}{|}}{\overset{R_1}{\overset{|}{C}}}\!\!-\!\!R_2$$

| Entry | Aldehyde/Ketone | Amine | Yield[a] (%) | Product | |
|---|---|---|---|---|---|
| 2 | 4-Cl-C₆H₄-CHO | HN(Et)₂ | 75 | [structure] | 1-(4-chlrophenyl)-N,N-diethylprop-2-yn-1-amine (D2) |
| 3 | 4-Br-C₆H₄-CHO | HN(Et)₂ | 80 | [structure] | 1-(4-bromophenyl)-N,N-diethylprop-2-yn-1-amine (D3) |
| 4 | 4-NC-C₆H₄-CHO | HN(Et)₂ | 76 | [structure] | 4-(1-(diethylamino)prop-2-ynyl)benzonitrile (D4) |
| 5 | 3,5-(MeO)₂-C₆H₃-CHO | HN(Et)₂ | 70 | [structure] | N,N-diethyl-1-(3,5-dimethoxyphenyl)prop-2-yn-1-amine (D5) |
| 6 | (CH₃)₂CHCHO | HN(Et)₂ | 71 | [structure] | N,N-diethyl-4,4-dimethylpent-1-yn-3-amine (D6) |

TABLE 4-continued

| Entry | Aldehyde/Ketone | Amine | Yield[a] (%) | Product |
|---|---|---|---|---|
| 7 | 3-phenylpropanal | diisopropylamine | 76 | N,N-diethyl-5-phenylpent-1-yn-3-amine (D7) |
| 8 | cyclohexanone | diethylamine | 68[b] | N,N-diethyl-1-ethynylcyclohexanamine (D8) |
| 9 | benzaldehyde | morpholine | 85 | 4-(1-phenylprop-2-ynyl)morpholine (D9) |
| 10 | benzaldehyde | pyrrolidine | 80 | 1-(1-phenylprop-2-ynyl)pyrrolidine (D10) |
| 11 | benzaldehyde | piperidine | 79 | 1-(1-phenylprop-2-ynyl)piperidine (D11) |
| 12 | benzaldehyde | diisopropylamine | 69 | N,N-diisopropyl-1-phenylprop-2-yn-1-amine (D12) |

TABLE 4-continued

| Entry | Aldehyde/Ketone | Amine | Yield[a] (%) | Product |
|---|---|---|---|---|
| 13 |  |  | 0 | |
| 14 |  |  | 0 | |

[a]Isolated yield.
[b]Reaction time was extended to 48 hours.

It is to be noted that no product was obtained when primary amines (see entries 13 and 14) were used.

Example 3

AAA-AHA-Coupling

A mixture of calcium carbide (1.2 mmol, 77 mg), benzaldehyde (1.0 mmol, 106 mg), diisopropylamine (2.5 mmol, 252 mg), and CuI catalyst (0.2 mmol, 40.0 mg) was added in a reaction tube (10 mL) with 4 mL CH$_3$CN. The reaction mixture was stirred for 18 hours at 80° C. followed by addition of dichloromethane (1.5 mmol, 126 mg) into the same reaction tube (that is, a "one-pot" reaction). After stirring at 80° C. for 24 hours the mixture was diluted with H$_2$O (10 mL), extracted with diethyl ether (2×10 mL), dried over Na$_2$SO$_4$ and concentrated under vacuum to give the crude product which was further purified by column chromatography on silica gel (ethyl acetate/hexane=4:1) to afford the corresponding pure asymmetric aminopropyne, N$^1$,N$^1$,N$^4$,N$^4$-tetraisopropyl-1-phenylbut-2-yne-1,4-diamine with an overall yield of 70%.

Example 4

AAA-Sonogashira-Coupling

A mixture of calcium carbide (1.2 mmol, 77 mg), benzaldehyde (1.0 mmol, 106 mg), diethylamine (1.5 mmol, 109.5 mg), and CuI catalyst (0.1 mmol, 20.0 mg) were added in the reaction tube (10 mL) with 4 mL CH$_3$CN. The reaction mixture was stirred for 18 hours at 80° C. and then followed by addition of iodobenzene (1.0 mmol, 204 mg), Pd(OAc)$_2$ (0.05 mmol, 11.2 mg) and Ph$_3$P (0.05 mmol, 13.1 mg) into the same reaction tube (that is, a "one-pot" reaction). After stirring at 60° C. for another 10 hours, the mixture was diluted with H$_2$O (10 mL), extracted with diethyl ether (2×10 mL), dried over Na$_2$SO$_4$ and concentrated under vacuum to give the crude product which was further purified by column chromatography on silica gel (ethyl acetate/hexane=4:1) to afford the corresponding propargylamine, N,N-diethyl-1,3-diphenyl-prop-2-yn-1-amine, with an overall yield of 66%.

Example 5

AAA-Click Chemistry

A mixture of calcium carbide (1.2 mmol, 80 mg), benzaldehyde (1.0 mmol, 106 mg), diethylamine (1.5 mmol, 151.5 mg), and CuI catalyst (20 mg, 10 mol %) was added into a reaction tube (10 mL) with 2 mL CH$_3$CN. After stirring at 80° C. for 72 hours (18 hours in case of undried CH$_3$CN), the mixture was diluted with H$_2$O (10 mL), the aqueous layers were extracted with diethyl ether (2×10 mL), dried over Na$_2$SO$_4$ and concentrated to give the crude product which was further purified by column chromatography on silica gel (ethyl acetate/hexane=1:4) to afford the corresponding pure propargylamine, N,N-diethyl-1-phenylprop-2-yn-1-amine, in 86% isolated yield.

Following this, a mixture of N,N-diethyl-1-phenylprop-2-yn-1-amine (0.5 mmol, 93.5 mg), sodium azide (0.6 mmol, 39 mg), Iodobenzene (0.5 mmol, 102 mg), CuI catalyst (10 mg, 10 mol %), and N,N-Dimethylethylenediamine (6.6 mg, 15 mol %) was added into the same reaction tube (10 mL) with 2 mL Dimethylformamide (that is, a "one-pot" reaction). After stirring at 40° C. for 12 hours, the mixture was diluted with H$_2$O (10 mL), the aqueous layers were extracted with diethyl ether (2×10 mL), dried over Na$_2$SO$_4$ and concentrated to give the crude product which was further purified by column chromatography on silica gel (ethyl acetate/hexane=1:4) to afford the decorated triazole product, N-ethyl-N-(phenyl (1-phenyl-1H-1,2,3-triazol-4-yl)methyl)ethanamine, with an isolated yield of 84%.

Example 6

Production of Enaminone

The reaction was conducted in an appropriate solvent with a copper halide catalyst (5 mol %) under mild conditions in one pot. Typical reaction conditions: benzaldehyde (1.0 mmol), calcium carbide (1.2 mmol), diisopropylamine (1.5 mmol), copper halide catalyst (0.05 mmol, 5.0 mol %), solvent (5.0 mL) and reaction temperature of 85° C. The different types of catalyst and solvent as well as the different reaction time are shown in Table 5 below. As can be seen in Table 5, an enaminone is produced when the solvent used is either dimethyl formamide (DMF) or dimethyl sulphoxide (DMSO). Other solvents used would result in the product of the aminopropyne.

TABLE 5

| Entry | Solvent | Catalyst (mol %) | Reaction Time (hours) | Yield (%) 2a | 2b |
|---|---|---|---|---|---|
| 1 | DMF (AR) | CuI (5) | 48 | 60 | 0 |
| 2 | DMSO (AR) | CuI (5) | 48 | 55 | 0 |
| 3 | CH₃CN (AR) | CuI (5) | 48 | 0 | 70 |
| 4 | THF (AR) | CuI (5) | 48 | 0 | 10 |
| 5 | Toluene (AR) | CuI (5) | 48 | 0 | 5 |
| 6 | DMF (5 ml) + H₂O (50 μL, 1.0%) | CuI (5) | 16 | 83 | 0 |
| 7 | DMF (5 ml) + H₂O (50 μL, 1.0%) | CuCl (5) | 16 | 15 | 0 |

TABLE 5-continued

| Entry | Solvent | Catalyst (mol %) | Reaction Time (hours) | Yield (%) 2a | 2b |
|---|---|---|---|---|---|
| 8 | DMF (5 ml) + H₂O (50 μL, 1.0%) | CuBr (5) | 16 | 78 | 0 |
| 9 | DMF (5 ml) + H₂O (50 μL, 1.0%) | CuOAc (5) | 16 | 5 | 0 |

AR: analytical reagent

Different types of aldehyde (1.0 mmol) as well as amine (1.5 mmol) were also tested as shown in Table 6 below. Unless otherwise stated, the catalyst used was 5 mol % copper iodide (CuI) (0.05 mmol), solvent was DMF (5.0 mL)+H₂O (50 μL), reaction time was 16 hours and the reaction temperature was 85° C.

TABLE 6

| Entry | Aldehyde | Amine | Enaminone (%)ᵃ | A³-Coupling (%)ᵃ |
|---|---|---|---|---|
| 1 | benzaldehyde | diisopropylamine | 83 | 0 |
| 2 | 4-methylbenzaldehyde | diisopropylamine | 74 | 0 |
| 3 | 4-ethylbenzaldehyde | diisopropylamine | 77 | 0 |

TABLE 6-continued

| Entry | Aldehyde | Amine | Enaminone (%)[a] | A³-Coupling (%)[a] |
|---|---|---|---|---|
| 4 | 3-methoxybenzaldehyde | diisopropylamine | 72 | 0 |
| 5 | 3,5-dimethoxybenzaldehyde | diisopropylamine | 70 | 0 |
| 6 | 4-phenylbenzaldehyde | diisopropylamine | 51 | 0 |
| 7 | 4-chlorobenzaldehyde | diisopropylamine | 85 | 0 |
| 8 | 4-bromobenzaldehyde | diisopropylamine | 87 | 0 |
| 9 | 4-cyanobenzaldehyde | diisopropylamine | 69 | 0 |
| 10 | 4-nitrobenzaldehyde | diisopropylamine | 65 | 0 |
| 11 | 4-(trifluoromethyl)benzaldehyde | diisopropylamine | 88 | 0 |

TABLE 6-continued

| Entry | Aldehyde | Amine | Enaminone (%)[a] | A³-Coupling (%)[a] |
|---|---|---|---|---|
| 12 | 3-phenylpropanal | diisopropylamine | 0 | 80 |
| 13 | benzaldehyde | pyrrolidine | <3 | 77 |
| 14 | benzaldehyde | diethylamine | <5 | 81 |
| 15 | benzaldehyde | N-methylisopropylamine | 49 | 40 |
| 16 | benzaldehyde | N-ethylisopropylamine | 90 | 0 |
| 17 | benzaldehyde | N-tert-butylisopropylamine | 69 | 0 |
| 18 | benzaldehyde | dicyclohexylamine | 92 | 0 |
| 19 | 4-methylbenzaldehyde | dicyclohexylamine | 78 | 0 |
| 20 | 4-ethylbenzaldehyde | dicyclohexylamine | 75 | 0 |

TABLE 6-continued

R¹-CHO + Ca(C≡C) + HNR²R³ →[CuI (5.0 mol %)][DMF (5 mL) + H₂O (50 uL), 95° C., 16 h] Enaminones (R¹-CO-CH=CH-NR²R³) + A³-Coupling (HC≡C-CHR¹-NR²R³)

| Entry | Aldehyde | Amine | Enaminone (%)[a] | A³-Coupling (%)[a] |
|---|---|---|---|---|
| 21 | 4-Cl-C₆H₄-CHO | dicyclohexylamine | 85 | 0 |
| 22 | 4-Br-C₆H₄-CHO | dicyclohexylamine | 86 | 0 |
| 23 | 3-MeO-C₆H₄-CHO | dicyclohexylamine | 82 | 0 |
| 24 | 3,5-(MeO)₂-C₆H₃-CHO | dicyclohexylamine | 78 | 0 |
| 25 | 4-O₂N-C₆H₄-CHO | dicyclohexylamine | 70 | 0 |

[a] isolated yield.

As observed, the use of amines that are bulkier than diethylamine resulted in the formation of enaminone, while the use of diethylamine (entry 14) resulted in the preferential production of the corresponding aminopropyne. Hence, in order to form the enaminone, the type of solvent and/or amine should be chosen appropriately.

In addition, when comparing between entries 11 and 12, the use of an aryl aldehyde (entry 11) resulted in the formation of the enaminone while the use of an alkyl aldehyde (entry 12) resulted in the formation of the aminopropyne. Hence, the choice of the aldehyde may also contribute to the product obtained.

Figure 1:
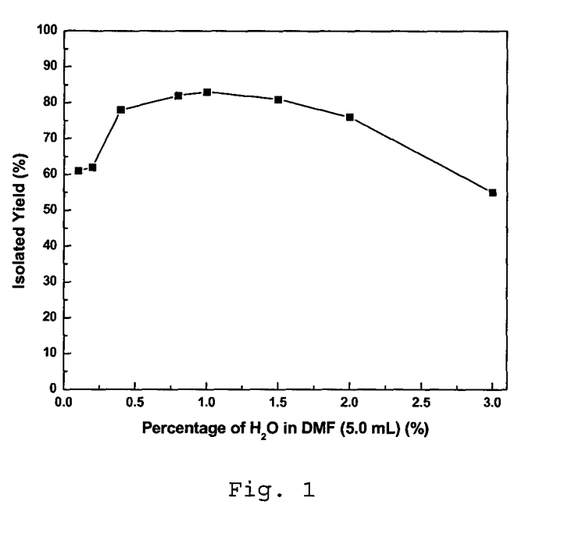
FIG. 1 is a graph showing the effects of water content in dimethyl formamide solvent on the yield of the isolated enaminone product.

A study on the effects of water content in the DMF solvent was also investigated. The reaction conditions are: benzaldehyde (1.0 mmol), calcium carbide (1.2 mmol), diisopropylamine (1.5 mmol), CuI (0.05 mmol, 5.0 mol %), DMF (5.0 mL)+H₂O (0 to 3.0%), reaction temperature of 85° C. and reaction time of 48 hours. The result of this study is shown in FIG. 1 which shows that the highest isolated yield was obtained when the solvent contained 1% of water.

Figure 2:
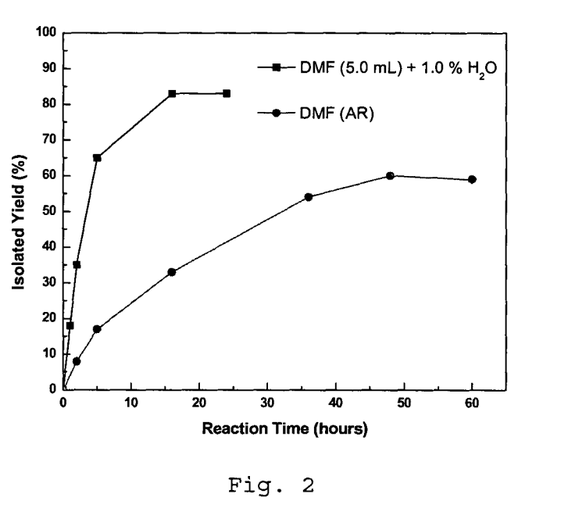
FIG. 2 is a kinetic study on the yield of the isolated enaminone product as a result of the reaction time under different solvent conditions.

Another study was carried out which was a kinetic study on the three-component coupling reactions of aldehydes, calcium carbide and amines to enaminones. Reaction conditions are: benzaldehyde (1.0 mmol), calcium carbide (1.2 mmol), diisopropylamine (1.5 mmol), CuI (0.05 mmol, 5.0 mol %), solvent used was either DMF (5.0 mL) (-●-) or DMF (5.0 mL)+H₂O (50 μL, 1.0%) (-■-) and reaction temperature was 85° C. The reaction time was varied from 0 to 24 hours (time points are 1, 2, 5, 16, 24 hours) for DMF+H₂O while that for DMF only was from 0 to 60 hours (time points are 2, 5, 16, 36, 48, 60 hours). The reactions were quenched at each time point by adding water.

Yields provided are of the isolated product. The result of this study is shown in FIG. 2 which shows that the highest isolated yield was obtained with DMF+H₂O.

Applications

The disclosed process may form aminopropynes with high yields and at mild conditions. The disclosed process may allow for the redevelopment of the application of a metal acetylide (such as calcium carbide) in organic synthesis.

Since the development that calcium carbide can be synthesized from lignocellulosic biomass, the low production costs of this method allows calcium carbide to better serve as a sustainable resource for the chemical industry. The use of calcium carbide in organic synthesis is more cost-efficient and safer that the use of traditional acetylene gas.

The mono-substituted aminopropyne obtained from the disclosed process can be used to produce other organic compounds such as an acetylamine or a triazol derivative. Hence, the reaction to produce complex alkynyl compounds from calcium carbide may be efficient, fast and simple.

Advantageously, due to the direct usage of calcium carbide, the need for numerous protection and de-protection steps may be greatly reduced, resulting in a more efficient and environmentally-friendly organic synthesis. Hence, calcium carbide can play a major role as a sustainable and cost efficient carbon source in modern organic synthesis.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A process for producing an aminopropyne comprising the step of reacting a metal acetylide, a primary or secondary amine and a ketone or an aldehyde in the presence of a transition metal catalyst;
   wherein:
   the metal acetylide is selected from the group consisting of calcium carbide ($CaC_2$), lithium acetylide ($Li_2C_2$) and lanthanium acetylide ($LaC_2$); and
   the transition metal of said transition metal catalyst is selected from the group consisting of copper, silver and gold; wherein when the transition metal is copper the transition metal catalyst is selected from the group consisting of copper chloride, copper bromide, copper iodide, copper fluoride, copper acetate and copper acetylacetonate.

2. The process as claimed in claim 1, wherein said aminopropyne has a terminal alkyne group.

3. The process as claimed in claim 1, wherein the aldehyde has the structure $R_1CHO$, where $R_1$ is selected from aryl or $C_{1-5}$-alkyl, said aryl being optionally substituted by at least one of halide, nitrile, $C_{1-5}$-alkyl, $C_{1-5}$-alkoxide, nitro and halo-$C_{1-5}$-alkyl and said $C_{1-5}$-alkyl being optionally substituted by phenyl; and the ketone has the structure $(R_2)_2CO$, where $R_2$ is selected from cyclic-$C_{3-6}$-alkyl.

4. The process as claimed in claim 1, wherein said amine is a secondary amine of the structure $R_3R_4NH$, where $R_3$ and $R_4$ are independently selected from $C_{1-5}$-alkyl; or wherein said amine is a heterocyclic secondary amine having 5 to 6 ring atoms.

5. The process as claimed in claim 1, wherein said reacting step is undertaken at a temperature from 50° C. to 150° C.

6. A process for producing a 1,2,3-triazole comprising the steps of:
   (a) reacting a metal acetylide, a primary or secondary amine and a ketone or an aldehyde in the presence of a transition metal catalyst to form an aminopropyne intermediate compound; and
   (b) adding sodium azide and any one of an aryl substituted with a halo group or a halo-$C_{1-5}$-alkane to said aminopropyne intermediate compound of step (a) to produce the 1,2,3-triazole;
   wherein:
   the metal acetylide is selected from the group consisting of calcium carbide ($CaC_2$), lithium acetylide ($Li_2C_2$) and lanthanium acetylide ($LaC_2$); and
   the transition metal of said transition metal catalyst is selected from the group consisting of copper, silver and gold; wherein when the transition metal is copper, the transition metal catalyst is selected from the group consisting of copper chloride, copper bromide, copper iodide, copper fluoride, copper acetate and copper acetylacetonate.

7. A process for producing an enaminone comprising the step of reacting a metal acetylide, an amine and an aldehyde in the presence of a transition metal catalyst;
   wherein:
   the metal acetylide is selected from the group consisting of calcium carbide ($CaC_2$), lithium acetylide ($Li_2C_2$) and lanthanium acetylide ($LaC_2$);
   the transition metal of said transition metal catalyst is selected from the group consisting of copper, silver and gold; wherein when the transition metal is copper, the transition metal catalyst is selected from the group consisting of copper chloride, copper bromide, copper iodide, copper fluoride, copper acetate and copper acetylacetonate; and
   wherein said amine is a secondary amine of the structure $R_5R_6NH$, where $R_5$ and $R_6$ is independently selected from $C_{1-5}$-alkyl and cyclo-$C_{3-6}$-alkyl; or wherein said amine is a heterocyclic secondary amine having 5 to 6 ring atoms.

8. The process as claimed in claim 7, wherein said aldehyde has the structure $R_1CHO$, where $R_1$ is selected from aryl, said aryl being optionally substituted by at least one of halide, nitrile, $C_{1-5}$-alkyl, $C_{1-5}$-alkoxide, nitro and halo-$C_{1-5}$-alkyl.

9. The process as claimed in claim 7, comprising the step of adding a solvent to said reacting step, said solvent being selected to induce formation of said enaminone.

10. The process as claimed in claim 9, wherein said solvent is a formamide or a sulphoxide.

* * * * *

UNITED STATES PATENT AND TRADEMARK OFFICE
CERTIFICATE OF CORRECTION

PATENT NO. : 9,193,668 B2  
APPLICATION NO. : 14/131083  
DATED : November 24, 2015  
INVENTOR(S) : Zhang et al.

Page 1 of 1

It is certified that error appears in the above-identified patent and that said Letters Patent is hereby corrected as shown below:

On The Title Page,

In Item (56), in column 2, under "Other Publications", line 29, delete "Dingyl," and insert --Dingyi,--, therefor.

In Item (57), in "Abstract", in column 2, line 8, delete "50° C. to 150° C." and insert --50 °C. to 150 °C.--, therefor.

In The Claims

In column 31, line 55, in Claim 5, delete "50° C. to 150° C." and insert --50 °C. to 150 °C.--, therefor.

Signed and Sealed this
Tenth Day of May, 2016

Michelle K. Lee
*Director of the United States Patent and Trademark Office*